United States Patent
Bruckheimer et al.

(10) Patent No.: US 6,482,222 B1
(45) Date of Patent: Nov. 19, 2002

(54) INTRAVASCULAR FILTER

(75) Inventors: Elchanan Bruckheimer, Zichron Yaacov (IL); Simon Brueckheimer, London (GB)

(73) Assignee: Rafael Medical Technologies Inc., Dover, DE (US)

( * ) Notice: Subject to any disclaimer, the term of this patent is extended or adjusted under 35 U.S.C. 154(b) by 96 days.

(21) Appl. No.: 09/613,760

(22) Filed: Jul. 11, 2000

(51) Int. Cl.[7] ............................................. A61M 29/00
(52) U.S. Cl. ....................................................... 606/200
(58) Field of Search ................................ 606/200, 191, 606/198, 194, 195, 159, 151, 1; 623/1.15, 1.1, 1.16–1.22, 1.54

(56) References Cited

U.S. PATENT DOCUMENTS

| | | |
|---|---|---|
| 4,425,908 A | 1/1984 | Simon |
| 4,494,531 A | 1/1985 | Gianturco |
| 4,619,246 A * | 10/1986 | Molgaard-Nielsen et al. ............ 128/899 |
| 4,643,184 A | 2/1987 | Mobin-Uddin |
| 4,793,348 A | 12/1988 | Palmaz |
| 4,832,055 A | 5/1989 | Palestrant |
| 4,957,501 A | 9/1990 | Lahille et al. |
| 4,969,891 A | 11/1990 | Gewertz |
| 4,994,069 A | 2/1991 | Ritchart et al. |
| 5,108,420 A * | 4/1992 | Marks ........................ 606/151 |
| 5,304,194 A | 4/1994 | Chee et al. |
| 5,531,788 A | 7/1996 | Dibie et al. |
| 5,601,595 A | 2/1997 | Smith |
| 5,649,906 A | 7/1997 | Gory et al. |
| 5,695,518 A | 12/1997 | Laerum |
| 5,700,258 A * | 12/1997 | Mirigian et al. ................ 606/1 |
| 5,797,953 A | 8/1998 | Tekulve |
| 5,836,969 A | 11/1998 | Kim et al. |
| 5,893,869 A | 4/1999 | Barnhart et al. |
| 5,928,260 A | 7/1999 | Chin et al. |
| 5,954,741 A | 9/1999 | Fox |
| 5,984,947 A | 11/1999 | Smith |

FOREIGN PATENT DOCUMENTS

EP            0121447           2/1984

* cited by examiner

*Primary Examiner*—Michael J. Milano
*Assistant Examiner*—(Jackie) Tan-Uyen T. Ho
(74) *Attorney, Agent, or Firm*—Mark M. Friedman

(57) ABSTRACT

An intravascular filter includes a first flexible elongated member configured to assume a generally helical form extending for at least about two turns about a central axis, and at least a second flexible elongated member connected to the first elongated member at at least two spaced apart connection positions chosen such that approximately equal lengths of the first and second flexible elongated members lie between the connection positions. The second elongated member is configured to assume a predefined filter form lying generally within the helical form in such a manner as to form an obstacle to passage through the substantially helical configuration, in a direction parallel to the central axis, of particles having dimensions greater than the predefined value. The first and second flexible elongated members are prepared in a generally straight configuration to facilitate minimally invasive deployment.

21 Claims, 6 Drawing Sheets

INTRAVASCULAR FILTER

FIELD AND BACKGROUND OF THE INVENTION

The present invention relates to intravascular devices deployable by minimally invasive techniques and, in particular, it concerns an intravascular filter which may be a stand-alone device or tethered to a guidewire, and is preferably easily retrievable.

The incidence of pulmonary embolism (PE) in the United States has been estimated at approximately 600,000 cases annually. Untreated PE carries a 30% incidence of mortality, which is decreased to 8% with anticoagulation. Although systemic anticoagulation remains the cornerstone of both treatment and prophylaxis for venous thromboembolism (VTE), permanent implantable endovascular filtering devices (i.e., caval filters, vena cava filters) are useful adjuncts for managing this disorder.

Although the concept of caval interruption to prevent embolization or propagation of proximal deep venous thrombosis (DVT) has been proposed since at least 1851, the first implantable endovascular devices for the treatment of VTE were the Mobbin-Uddin Umbrella and the Kimray-Greenfield filter. Like their modern counterparts, these devices were designed to filter and trap thrombi that could result in a lung embolus. Their design allowed filtering to occur without occlusion of the venous return. A number of devices have since been introduced and original designs have undergone significant technical refinements. Most devices are made of fatigue-resistant stainless steel or titanium alloys and are compatible with magnetic resonance MRI techniques. In contrast to the surgical cutdown required to place early caval filters, nearly all filters now are deployed via a percutaneous catheter-guided method under fluoroscopic guidance.

Vena cava filters (VCFs) are typically positioned within the infrarenal inferior vena cava (IVC) to trap thrombi arising from the lower extremities, avoiding potential occlusion of the renal veins. Limited reports also document the successful use of caval filters in the superior vena cava, as well as in the suprarenal IVC.

Both fatal and nonfatal complications have been reported for VCFs. Fatal or serious nonfatal complications are rare. Improved safety profiles and favorable experience with these devices have led a number of authors to advocate broader indications for the placement of caval filters, although many proposed indications remain controversial.

The number of VCFs placed annually has dramatically increased since the availability of the transcatheter delivery system, leading some authors to speculate that many filters may be placed without appropriate indications. Our experience in a major teaching hospital, consistent with many other reports, suggests that most VCF use is for what would be generally agreed upon as standard indications.

There are six permanent caval filters, representing four major design types, available for use in the United States. These are shown in FIG. 9 as: (A) stainless steel Greenfield; (B) modified hook titanium Greenfield; (C) alternating hook stainless steel Greenfield; (D) Bird's Nest; (E) Vena Tech; and (F) Simon-Nitinol.

The Greenfield filter (Medi-Tech/Boston Scientific Corp; Watertown, Mass.) was introduced in 1973. Three designs have been approved by the Food and Drug Administration for patient use in the United States. The original stainless steel cone-shaped design allowed 70 and 80% of the volume of the device to be filled with clot without a significant reduction in blood flow and was designed for a maximal caval diameter of $\leq 2.8$ cm. The original stainless steel Greenfield filter was introduced through a relatively large 26F sheath and, due to its composition, led to significant artifact on MRI. It has been shown to be resistant to dislodgment at MRI field strengths of 1.5 T. This initial design was refined to a titanium "modified hook" Greenfield filter, which was contained within a smaller 14F sheath, facilitating percutaneous placement and causes no artifacts on MRI. The original stainless steel design was also recently modified to allow insertion over a guidewire through a smaller 12F sheath. It also has alternating hook arrangements. These two later designs may be safely accommodated within a larger caliber IVC.

The Gianturco-Roehm Filter, commonly known as the Bird's Nest filter (Cook Corp; Bloomington, Ind.), consists of two V-shaped struts supporting a random tangle of stainless steel wire. It was introduced in 1984. Stable placements of this filter in vessels up to 4 cm have been reported. The Bird's Nest filter is placed through a small sheath (14F), allowing for percutaneous placement through the femoral, internal jugular, or antecubital routes. One drawback of the Bird's Nest filter is a significant image artifact with abdominal MRI. Safety in a 1.5-T MRI field has been demonstrated with no significant device migration.

The Simon-Nitinol filter (Nitinol Medical Technologies; Woburn, Mass.) is introduced through the smallest sheath (9F) of all the designs available in the United States, allowing for introduction via an antecubital or the external jugular vein. This filter has a unique composition (nickel-titanium alloy) that assumes a preformed shape when warmed, but is pliable when cooled. This alloy is compatible with MRI and creates only minor local artifacts.

The Lehmann-Girofflier-Metais filter, referred to as the Vena Tech filter (B. Braun; Vena Tech; Evanston, Ill.) in the United States, is a derivation of a conical filtering device with anchoring longitudinal side rails. These serve to center the device in the vessel, thereby decreasing malalignment. The original design, introduced in 1986, was modified because of incomplete opening, caudal migration, and decreased clot trapping ability. The currently used Vena Tech cone and side rail lengths are approximately equal and are contained within a 12.9F sheath. The filter is made from an eight-metal alloy with a low ferromagnetic moment, which does not cause significant artifact on MRI.

The efficacy of caval filters may be affected by positioning. The filter may be malpositioned within the lumen of the IVC (i.e., tilted), thus reducing the effective filtering capacity of the device. All devices, with the exception of the Bird's Nest filter, are subject to tilting. An in vitro study has suggested that clot trapping can be decreased in the Greenfield or Vena Tech filter if the degree of tilt is >15 degrees. The incidence of significant tilting of these two filter types has been reported as 1.7% and 1 to 2% respectively. On the other hand, Simon-Nitinol filters show no decrease in clot trapping efficiency when tilted up to 20 degrees. Although the reported cases are few, evidence is accumulating that recurrent PE after VCF placement may be associated with tilted devices.

The Bird's Nest filter, by virtue of its design, is subject to wire prolapse proximal to the anchoring struts. The incidence of wire prolapse is reported as 11%.

One of the factors thought to be responsible for the relatively slow adoption of intravascular filters into use is the non-retrievability of the available devices. This leads to problems during deployment where the initial alignment is incorrect, and generally requires the filters once deployed to be left in place indefinitely.

A further complication associated with these devices is penetration of tissues by the retaining hooks of the devices. Penetration of the retaining hooks of the filter through the lumen of the IVC is necessary for the proper anchoring of the device. Further penetration of these struts is commonly seen on radiographs, reported in at least about 10% of cases. In extreme cases, such over penetration may impinge upon adjacent organs, leading to serious or even fatal complications.

In an attempt to reduce risks of perforation, a number of recent developments have employed rounded wire structures which become lodged within the blood vessel. Examples of this type may be found in European Patent Application Publication No. EP 121447, and U.S. Pat. Nos. 4,957,501 and 5,531,788. These devices all function primarily by asymmetric stretching of the blood vessel so as to reduce its cross-sectional area. The wire formations proposed are generally ineffective as filters.

A further problem of many devices to accommodate the relatively rapid variations in size of the blood vessels occurring during breathing, coughing, straining and the like. Failure to expand properly may lead to impaired filtering function and/or dislodging of the device. Failure to contract may damage the vessel wall.

In summary, all of the currently available intravascular filter devices suffer from one or more of a range of shortcomings including: risk of migration or dislodging of the device; risk of trauma to, or perforation of, the blood vessel; failure to accommodate variations in vessel size; and unreliable filtering performance.

Another field of application of the present invention is for distal prevention to avoid strokes. Stroke is a form of cardiovascular disease that interrupts blood flow to the brain. A stroke occurs when a branch of the carotid artery leading to the brain becomes clogged (ischemic stroke) or bursts (hemorrhagic stroke), preventing oxygen-rich blood from reaching the brain. As a result, brain cells die. Once dead, they do not regenerate which is why damage from a stroke is frequently permanent. Stroke accounts for 10% to 12% of all deaths in industrialized countries. For example, in a population of one million, 1,600 people will have a stroke each year, of which only 55% will survive six months post-stroke, and a third of the survivors will have significant disability. Stroke ranks third in terms of leading causes of death in the United States, behind heart disease and cancer. Strokes cause an estimated 150,000 deaths each year and are the leading cause of long-term disability. Current treatment options include medical management (drug therapy), carotid endarterectomy, or stent-supported carotid angioplasty. Carotid endarterectomy has demonstrated a marked increase in its use during the past two years on the basis of pivotal studies demonstrating a reduction in stroke after carotid revascularization. It is well documented that carotid endarterectomies have a 3% to 6% complication rate, depending if the patient is asymptomatic or symptomatic.

Embolization has represented an obstacle to widespread acceptance of stent-supported carotid angioplasty due to the brain's sensitivity to even small amounts of emboli, with clinically significant strokes occurring in the absence of angiographically definable branch vessel occlusions. If stent-supported carotid angioplasty is to compete effectively against the endarterectomy, it must demonstrate equal complication rates. In particular, carotid angioplasty must not lead to an increase in embolization or stroke rates.

Industry sources estimate roughly 100,000 carotid endarterectomies were performed in the United States alone in 1997. In the same year, approximately 90,000 procedures were performed internationally and are increasing at a faster rate than the United States. The desire among patients to have—and cardiologists to perform—less invasive procedures is evident. Industry estimates indicate that the number of carotid angioplasty procedures in the United States will grow from roughly 3,000 in 1998 to approximately 36,000 procedures in 2002. If the risk of embolization were reduced, this trend would develop much faster and fewer patients would require endarterectomy.

To reduce the risk of embolization during angioplasty, it has been proposed to deploy a temporary distal protection device associated with the end of a guidewire to catch any emboli resulting from the angioplasty procedure. The only commercially available devices offering such functionality are devices based upon inflatable balloons.

For completeness, reference is made briefly to U.S. Pat. No. 5,893,869 to Barnhart et al. which discloses a system for removing emboli from the blood flow. The device includes a conical filter funnel formed by an inwardly spiraling wire which funnels large particles towards an opening in the delivery catheter. The device is not a free-standing filter, being usable only while the catheter is inserted, and can only be used to trap emboli travelling towards the catheter.

There is therefore a need for an effective intravascular filter which could be deployed and removed by minimally invasive techniques, which would readily accommodate variations in size of the blood vessel, and which would minimize or eliminate the risks of perforation of the vessel wall.

SUMMARY OF THE INVENTION

The present invention is an intravascular filter for minimally invasive deployment within a blood vessel so as to obstruct the passage of particles of dimensions greater than a predefined value through the blood vessel.

One aspect of the present invention is a particle filter intended to be inserted in vessels of a living being by a tailored delivery system, not involving significant surgery, arranged to be held in such a position to prevent significantly sized particulate from reaching and damaging vital tissues downstream of fluid flow.

A further aspect of preferred implementations of the present invention is that it is fully retrievable by similar tailored means, not involving significant surgery, when the danger of such particulate has abated.

A further aspect of preferred implementations of the present invention is that it ensures no significant damage to the vessel into which it is inserted by distributing diffuse pressure evenly across a large area of the vessel wall.

A further aspect of preferred implementations of the present invention is that selectively it may be designed to dilate rapidly when the containing elastic vessel dilates under momentary stress conditions, thereby maintaining an evenly distributed pressure on the vessel walls so as to prevent displacement, by use of the superelastic properties of the materials from which it is constructed.

A further aspect of preferred implementations of the present invention is that it is formed from material that has both shape memory and superelastic properties, which enable it to be introduced into a living organism with a minimal profile and size of entry point, follow an arbitrarily tortuous path in that organism to the required position, and recover its desired profile and properties in a fully reversible manner.

A further aspect of preferred implementations of the present invention is that it may be constructed and stored as a strip which may be made in various lengths and sizes, or can be made in a manner that it can be cut to length to suit the dimensions of a particular application, those dimensions being unconstrained and serving the widest range of applications.

Thus, according to the teachings of the present invention there is provided, an intravascular filter for minimally invasive deployment within a vessel so as to obstruct the passage of particles of dimensions greater than a predefined value through the vessel, the intravascular filter comprising: (a) a first flexible elongated member configured to assume a substantially helical form extending for at least about one turn about a central axis; and (b) at least a second flexible elongated member connected to the first flexible elongated member at at least two spaced apart connection positions chosen such that approximately equal lengths of the first and second flexible elongated members lie between the connection positions, the second flexible elongated member being configured to assume a predefined filter form lying substantially within the substantially helical form in such a manner as to form an obstacle to passage through the substantially helical configuration, in a direction parallel to the central axis, of particles having dimensions greater than the predefined value.

According to a further feature of the present invention, at least one of the first and second flexible elongated members is attached to, or integrally formed with, a guidewire in such a manner that the intravascular filter can be drawn into a catheter by withdrawal of the guidewire.

According to a further feature of the present invention, the predefined filter form is substantially angularly periodic about the central axis.

According to a further feature of the present invention, the predefined filter form includes a plurality of lobes angularly spaced around the central axis.

According to a further feature of the present invention, the substantially helical form approximates to a helix modulated by an undulating pattern having a maximum amplitude not significantly greater than a diameter of the helix.

According to a further feature of the present invention, the first flexible elongated member is formed with a plurality of small longitudinal slits and is configured to open up the slits to form a latticework type effect when in the substantially helical form.

According to a further feature of the present invention, the first and second flexible elongated members are formed as an elongated flat strip subdivided along its length by an elongated slit except at the connection positions.

According to a further feature of the present invention, the first and second flexible elongated members are formed as two lengths of wire connected together at the connection positions.

According to a further feature of the present invention, the first and second flexible elongated members are formed primarily from a super elastic alloy, the first and second flexible elongated members being elastically biased to the substantially helical form and the filter form, respectively, and being elastically deformable into a substantially straight configuration in which the first and the second flexible elongated members are substantially straight to facilitate minimally invasive deployment.

According to a further feature of the present invention, the first and second flexible elongated members are formed primarily from a shape-memory material, the first and second flexible elongated members being set to the substantially helical form and the filter form, respectively, and being subsequently deformed to provide a substantially straight configuration in which the first and the second flexible elongated members are substantially straight to facilitate minimally invasive deployment.

According to a further feature of the present invention, subsequent to a transition from the substantially straight state to the pre-set state, the first and second flexible are deformable so as to return to a substantially straight state to facilitate minimally invasive retrieval.

According to a further feature of the present invention, the first and second flexible elongated members are formed primarily from Nitinol.

According to a further feature of the present invention, there is also provided at least a third flexible elongated member connected to the first flexible elongated member at at least two spaced apart connection positions chosen such that approximately equal lengths of the first and third flexible elongated members lie between the connection positions, the third flexible elongated member being configured to assume an additional predefined filter form lying substantially within the substantially helical form and configured to complement the filter form of the second elongated member so as to form an enhanced obstacle to passage through the substantially helical configuration, in a direction parallel to the central axis, of particles having dimensions greater than the predefined value, wherein the first, second and third flexible elongated members are prepared in a substantially straight configuration to facilitate minimally invasive deployment.

There is also provided according to the teachings of the present invention, an intravascular filter for minimally invasive deployment within a vessel so as to obstruct the passage of particles of dimensions greater than a predefined value through the vessel, the intravascular filter comprising: (a) a first flexible elongated member configured to assume a substantially helical form extending for at least about one turn about a central axis; and (b) second and third flexible elongated members, each connected to the first flexible elongated member at at least two spaced apart connection positions, wherein the second flexible elongated member is configured to assume a first predefined filter form lying substantially within the substantially helical form and the third flexible elongated member is configured to assume a second predefined filter form lying substantially within the substantially helical form, the first and second predefined filter forms together forming an obstacle to passage through the substantially helical configuration, in a direction parallel to the central axis, of particles having dimensions greater than the predefined value.

According to a further feature of the present invention, the first predefined filter form is substantially angularly periodic with a first angular period about the central axis and the second predefined filter form is substantially angularly periodic with a second angular period about the central axis, the second angular period differing from the first angular period.

According to a further feature of the present invention, the first, second and third flexible elongated members are formed as an elongated flat strip subdivided along its length by two elongated slits except at the connection positions.

According to a further feature of the present invention, the first, second and third flexible elongated members are formed as three lengths of wire connected together at the connection positions.

According to a further feature of the present invention, the first, second and third flexible elongated members are formed primarily from a super elastic alloy, the first, second and third flexible elongated members being elastically biased to the substantially helical form and the first and second filter forms, respectively, and being elastically deformable into a substantially straight configuration in which the first, second and third flexible elongated members are substantially straight to facilitate minimally invasive deployment.

According to a further feature of the present invention, the first, second and third flexible elongated members are formed primarily from a shape-memory material, the first, second and third flexible elongated members being set to the substantially helical form and the first and second filter forms, respectively, and being subsequently deformed to provide a substantially straight configuration in which the first, second and third flexible elongated members are substantially straight to facilitate minimally invasive deployment.

There is also provided according to the teachings of the present invention, a method for preparing an intravascular filter for use, the method comprising: (a) providing an elongated strip including: (i) a first flexible elongated member configured to assume a substantially helical form extending for a plurality of turns about a central axis, and (ii) at least a second flexible elongated member connected to the first flexible elongated member at at least one connection position per turn of the helical form, the connection positions being chosen such that approximately equal lengths of the first and second flexible elongated members lie between the connection positions, the second flexible elongated member being configured to assume a predefined filter form lying substantially within the substantially helical form in such a manner as to form an obstacle to passage through the substantially helical configuration, in a direction parallel to the central axis, of particles having dimensions greater than he predefined value, wherein the first and the second flexible elongated embers are prepared in a substantially straight configuration to facilitate minimally invasive deployment; and (b) cutting the elongated strip to separate a given length of the elongated strip to provide an intravascular filter ready for minimally invasive deployment.

BRIEF DESCRIPTION OF THE DRAWINGS

The invention is herein described, by way of example only, with reference to the accompanying drawings, wherein:

FIG. 5A is a schematic isometric view of a helical elongated member from the intravascular filter of FIG. 1;

FIGS. 54B–5D are schematic enlargements of a circled portion of FIG. 5A illustrating a number of optional features of the elongated member of FIG. 5A;

DESCRIPTION OF THE PREFERRED EMBODIMENTS

Figure 1:
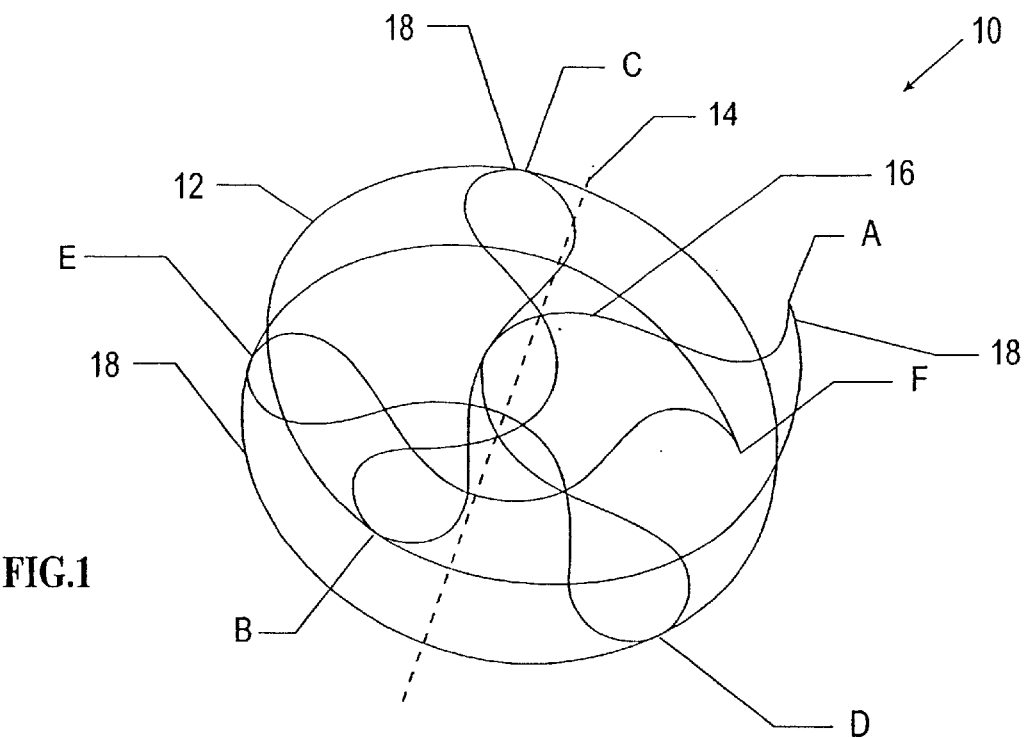
FIG. 1 is a schematic isometric view of an intravascular filter constructed and operative according to the teachings of the present invention.

The present invention is an intravascular filter for minimally invasive deployment within a blood vessel so as to obstruct the passage of particles of dimensions greater than a predefined value through the blood vessel.

The principles and operation of intravascular filters according to the present invention may be better understood with reference to the drawings and the accompanying description.

Referring now to the drawings, FIGS. 1–5 show an intravascular filter, generally designated 10, constructed and operative according to the teachings of the present invention, for minimally invasive deployment within a blood vessel so as to obstruct the passage of particles of dimensions greater than a predefined value through the blood vessel.

In general terms, intravascular filter 10 includes a first flexible elongated member 12 configured to assume a substantially helical form (FIGS. 1 and 2) extending for at least about one, and preferably at least about two, turns about a central axis 14, and at least a second flexible elongated member 16 connected to first elongated member 12 at at least two spaced apart connection positions 18 chosen such that approximately equal lengths of the first and second flexible elongated members lie between the connection positions. Second elongated member 16 is configured to assume a predefined filter form (FIGS. 1 and 2) lying substantially within the substantially helical form in such a manner as to form an obstacle to passage through the substantially helical configuration, in a direction parallel to the central axis, of particles having dimensions greater than the predefined value. First and second flexible elongated members 12 and 16 are prepared in a substantially straight configuration (FIG. 4) to facilitate minimally invasive deployment.

In addition to providing a highly advantageous stand-alone IVC filter structure, a further important application of the filters of the present invention employs a filter tethered to a guidewire as a distal protection device during procedures such as stenting of the carotid artery, angioplasty in renal arteries, and saphenous venous grafts. In this case, a smaller dimension filter is preferably attached to, or integrally formed with, the end of the guide wire. The filter is deployed distally of the procedure site and remains in place throughout performance of the procedure, catching any debris which may be released. At the end of the procedure, the filter is withdrawn, together with any material which was trapped, into a sheath which has been advanced through the stent.

A further highly advantageous property of preferred implementations of the present invention is that they are fully and readily retrievable. This feature offers profound advantages, both in terms of immediate redeployment during installation where the initial alignment is not as required, and for late retrieval when the device is no longer required within the vessel.

It should be understood that intravascular filter 10 may be made from a wide variety of flexible materials including, but not limited to, polymer materials and various metal alloys. In one set of preferred implementations, superelastic alloys are employed to provide sufficient flexibility to allow gross deformation of the filter during deployment without compromising its ability to reassume the desired shape. This allows the filter to be deployed through a tailored delivery means which has a very small profile compared to the filter's dimensions when deployed, and also permits retrieval by similar or identical means. In this case, first and second elongated members 12 and 16 are formed primarily from a super elastic alloy elastically biased to their intended substantially helical form and filter form, respectively. The elongated members are then elastically deformable into the substantially straight configuration in which they are maintained within a catheter prior to delivery.

According to an alternative preferred implementation, shape-memory materials are employed. This allows temporary unstressed storage of the device in a straightened deformed state prior to use. Then, during deployment, a state change induced by the host environment, through for example a change in temperature, causes the filter to revert to the previously defined desired shape. This further facilitates delivery of the filter through a very small profile tailored delivery means which has a particularly small profile compared to the filter's dimensions when deployed. As a result, the filter can typically be deployed by use of a 5 or 6 French catheter, which is significantly smaller than most of the delivery configuration for the smallest currently available intravascular filters. A particularly preferred example of a class of materials suitable for providing a combination of shape memory and superelastic properties is Nickel-Titanium alloys, known as Nitinol, which are also relatively inert in living tissue. A full discussion of the properties and design considerations for constructing devices from Nitinol may be obtained from numerous sources such as, for example, via an internet page entitled "Nitinol Technical Information" at http://www.sma-inc.com/information.html, and its associated links, provided by Shape Memory Applications, Inc. of San Jose, Calif.

Practically speaking, for a shape-memory implementation, first and second members 12 and 16 are formed primarily from a shape-memory material set to the substantially helical form and the filter form, respectively. The elongated members are subsequently deformed to provide the substantially straight configuration for storage and deployment via a small profile delivery system.

Turning now to the structural details of first elongated member 12, this acts as a helical backbone of the filter, providing a number of critical benefits as will now be detailed. Firstly, the helix is a natural transformation from a linear disposition, providing an even distribution of the filter components along a predefined length, both in the stretched-out linear state and the helical deployed state. This avoids folding and overlap of materials which are prevalent in many other filter designs that compress into shorter lengths and which lead to much more bulky structures requiring a larger deployment means and causing greater disruption to the organism's vessels.

Secondly, the helix-to-linear transformation is reversible, readily allowing retrieval of the filter by a similar or even identical means as used for deployment.

Thirdly, the linear configuration allows an arbitrary length of filter material to be manufactured and cut from stock to provide a desired density of cross-pieces in the deployed filter, thereby allowing tailored adjustment of the filtering capability to the application. According to one advantageous implementation, the angular frequency of cross-pieces may be straightforwardly designed to be relatively prime to 360 degrees, ensuring non-coincidence of cross-pieces over a widely selectable range of revolutions of the helix, in manufacture and deployment alike, as will be described further below.

Additionally, the continuous form of the helical backbone ensures an evenly distributed frictional retaining pressure of the filter on a vessel's walls, thereby minimizing the risk of damage. Many other filter designs usually apply point pressure which has a high risk of puncturing the vessel in deployment, use, and retrieval (if the latter is at all possible).

The helical backbone has further advantages in its ability to expand against the vessel's inner walls, and exert a certain amount of pressure in order to retain its positioning, even as the vessel elastically dilates. The amount of acceptable vessel dilation accommodated may be tailored by the dimensions and material selected for the filter. In practice the unrestricted diameter of the filter is chosen to be a defined amount larger than the diameter of the vessel into which it is introduced such that the inherent springiness and constancy of stress of superelastic materials exerts an approximately constant force, even as the vessel dilates. It is anticipated that considerable diametric dilation can be accommodated in this manner.

In certain preferred implementations, first elongated member 12 is modified to further increase its ability to accommodate variations in diameter. Specifically, in a preferred modification, the "substantially helical form" of first elongated member 12 approximates to a helix modulated by a wavy pattern having a wave amplitude and period not significantly greater than, and typically smaller than, a diameter of the helix. This is illustrated in FIG. 5B. In one preferred example, the crests of the waves, i.e., the portions of the wave form most "upstream" relative to the flow direction, coincide with the points at which the cross-pieces join the backbone.

This modification provides several additional benefits. Firstly, unlike a simple helix where variations in diameter are accommodated primarily by sliding across the internal walls of the vessel, the modified undulating form can accommodate variations by flexing of the wavy shape, i.e., by the crests of the wave moving apart while the amplitude of the wave decreases. Thus, the backbone no longer needs to slide and can maintain its contact with the vessel, reducing the chance of it becoming dislodged. The wavy path may also be helpful in increasing the length of the backbone and, concomitantly, the approximately matched length of the cross-pieces of second member 16 between joins.

Another preferred feature, which may be used alone or in combination with the aforementioned undulations, is the use of a first member 12 formed with a plurality of small longitudinal slits which are configured to open up to form a latticework type effect when in the substantially helical form (FIGS. 5C and 5D). The latticework type effect may be confined to troughs where an undulating path is used, or over any greater length as appropriate. The spaces in the latticework effect permit the elastic vessel wall to bow inwards, trapping tissue between the lattice wires. It also distributes the frictional retention force over a yet greater area of the vessel.

Turning now to the features of second elongated flexible member 16 in more detail, the predefined filter form is preferably substantially angularly periodic about the central axis. This is considered helpful in minimizing the amount of fluid turbulence caused by the filter. The cross-section of the cross-pieces may also be selected to provide a low drag coefficient to minimize turbulence, or indeed may be arranged to twist or otherwise modify fluid flow to control turbulence, where this is important.

The predefined filter form assumed by second member 16 preferably includes a plurality of lobes angularly spaced around central axis 14. Preferably, these lobes extend close to, and most preferably overlap, the axis, thereby providing effective filter coverage of the central portion of the vessel. The overlap of the axial region is considered particularly advantageous since it ensures that any further dilation of the blood vessel brings the filtering elements closer to, rather than more distant from, the axis, thereby maintaining effective filter coverage of the critical central portion.

As mentioned above, the angular frequency of the cross-pieces is preferably chosen to ensure non-coincidence of cross-pieces over a widely selectable range of revolutions of the helix. More specifically, the predefined filter form of second elongated member 16 is preferably substantially angularly periodic about central axis 14 with a period of approximately $2\pi n/p$ radians where p is a positive integer no less than 3, n is a positive integer smaller than p, and p and n are relatively prime. However, combinations without this restriction may be of use in certain applications, and those skilled in the art will appreciate that the construction of the filter from two members in the manner described above is not inherently limited to a periodic or symmetrical distribution. Most preferably, p is chosen to be 5 or 7 and n is chosen to be 2 or 3. In the specific example illustrated in FIGS. 1 and 2, p is 5 and n is 2. An example in which p is 7 and n is 2 or 3 will be discussed below with reference to FIG. 6. To ensure a full, roughly symmetrical filtering pattern, n should be an integer, corresponding to a complete number of turns of the helical backbone.

It should be noted that the aforementioned geometrical relations are idealized and may only hold approximately true when the filter is deployed within a vessel of a particular intended size in a slightly constricted state. For the purpose of the description and claims, such variations are still regarded as having "a period of approximately $2\pi n/p$ radians".

Figure 2:
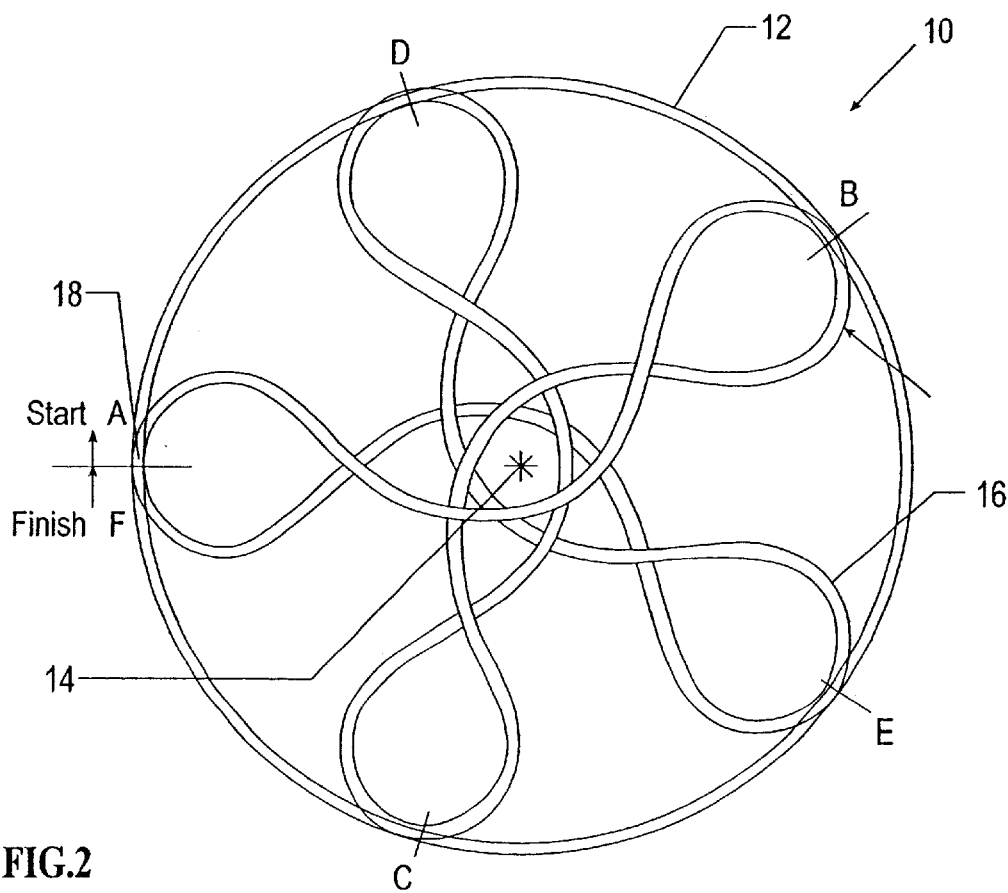
FIG. 2 is a plan view of the intravascular filter of FIG. 1.
Figure 3:
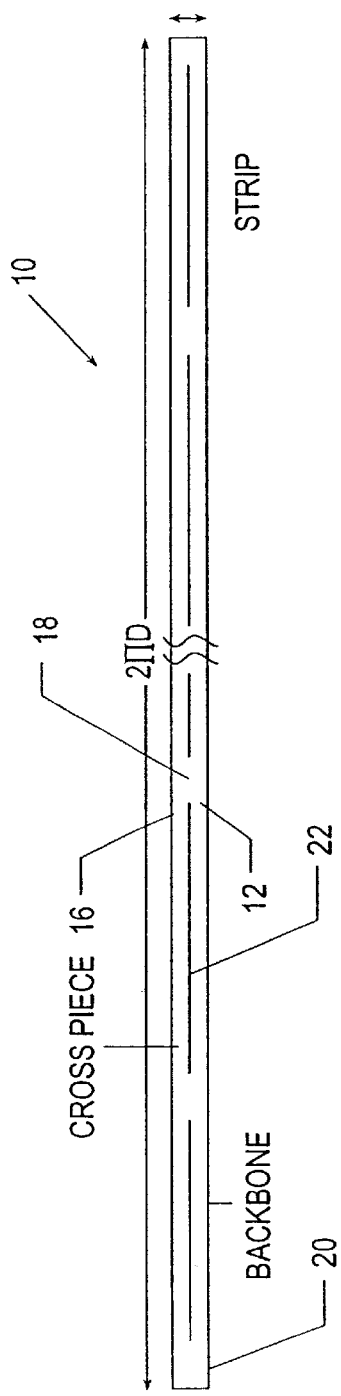
FIG. 3 is a schematic plan view of the device of FIG. 1 prepared as a straight strip prior to deployment.
Figure 4:
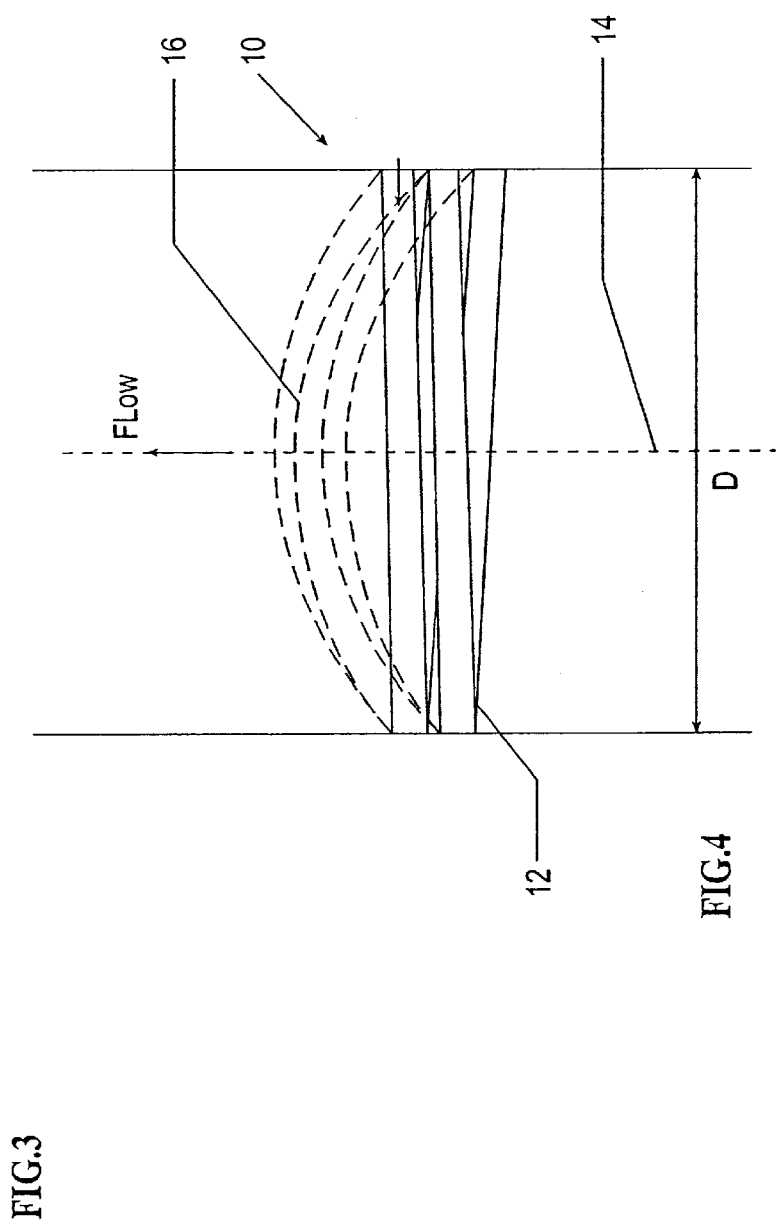
FIG. 4 is a schematic cut-away side view of the intravascular filter of FIG. 1 deployed within a blood vessel.
Figure 5:
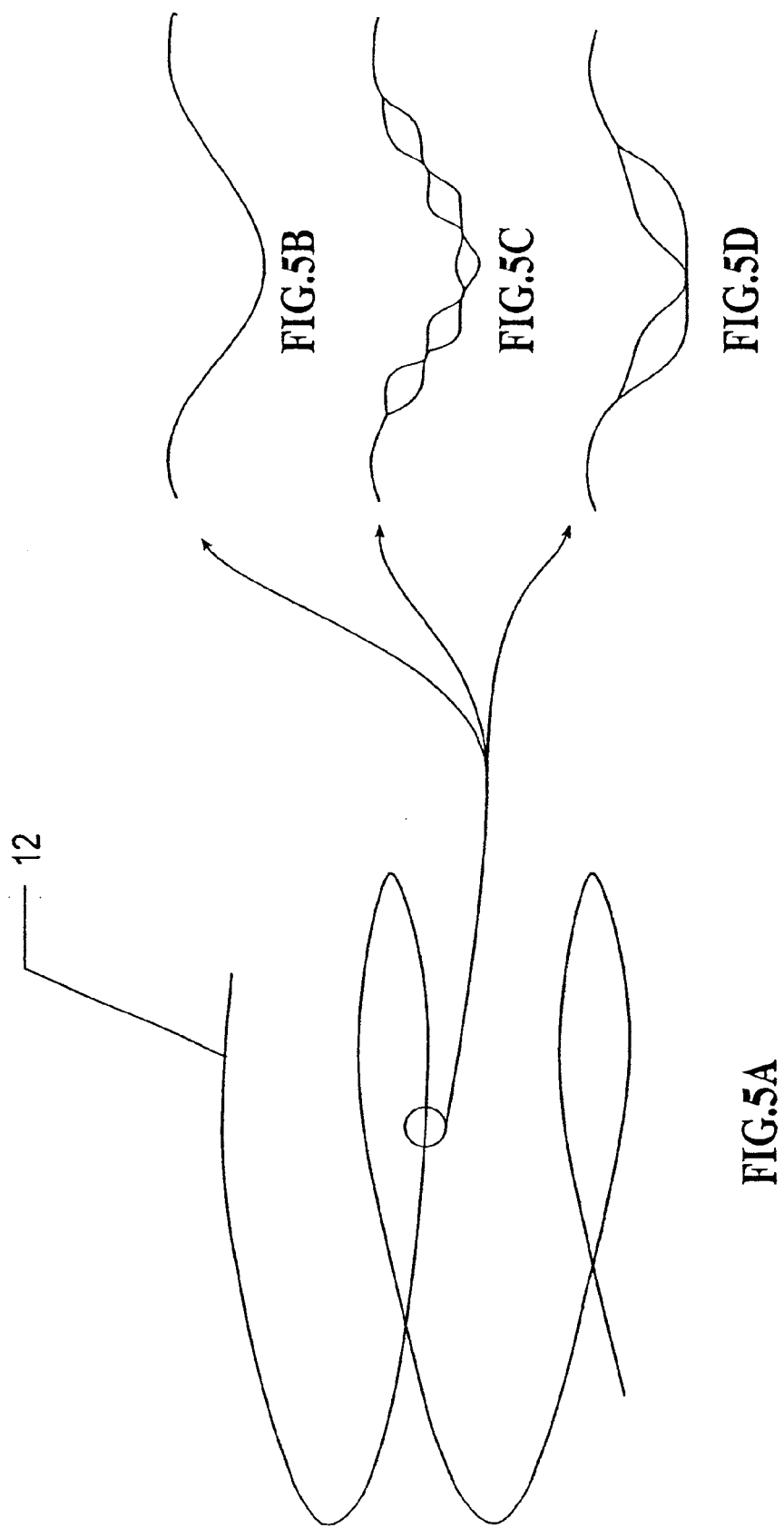

Referring specifically to FIGS. 1 and 2, the preferred filter pattern may be seen to follow a path which, in plan view, exhibits approximately pentagonal symmetry. The points of connection 18 to first elongated member 12 are identified sequentially by letter A–F, spaced around two turns of the helical backbone. Points A, B and C lie on the first turn, while points D, E and F lie on the second. The angular spacing of these points about axis 14 is approximately $4\pi/5$ radians (144°). This configuration is believed to be effective to provide a filter for particles in the range of about 3–4 mm for a blood vessel of diameter up to about 20 mm. For larger vessels, a relatively denser filtering pattern may be required, such as that described below with reference to FIGS. 6 and 7. The points of connection 18 may selectively also be a subset of the points A–F. Furthermore, the filter member 16 may lie substantially within the diameter of the backbone member 12, and only extend out to the member 12 where connected 18.

As mentioned earlier, the lobes of the filter form assumed by member 16 preferably overlap the central axis 14 such that coverage of the central region is not diminished by dilation of the blood vessel. In another geometrical consideration, the filter form is preferably roughly tangential to the outer helix near points of connection 18. This minimizes stress on the material, and facilitates compact parallel positioning of the elongated members in their straightened state, and allows them to slide freely inside a catheter.

As discussed above, filter 10 is most preferably formed from a shape memory, superelastic alloy, most preferably Nitinol. Attachment of such materials to themselves and other materials is often somewhat problematic, tending to cause local disruption to the properties of the material. To avoid this problem, according to one particularly preferred set of implementations of the present invention (FIGS. 3 and 7), the two or more flexible elongated members are formed as an elongated flat strip 20 subdivided along its length by one or more elongated slit 22 except at connection positions 18.

In an alternative set of implementations, the flexible elongated members are formed as two lengths of wire which are connected together at the connection positions. The two lengths of wire may be a single longer wire folded in the middle, thereby providing one connection inherently. The remaining connections may be achieved by known techniques suited for attachment of the wire material to itself. Preferred connecting techniques include, but are not limited to, various welding procedures and crimping the wires together by use of an externally applied connector element. It should be noted that, where the joining technique may compromise the properties of the material, the number of connection positions 18 may be reduced to the minimum required to ensure proper positioning of the filter element relative to the helical backbone. In most cases, three connections will suffice for this purpose. Nevertheless, additional connections may be valuable in that they help to maintain proper positioning and even distribution of the lobes of the filter element, which is vital to achieve uniform filtering properties.

Figure 6:
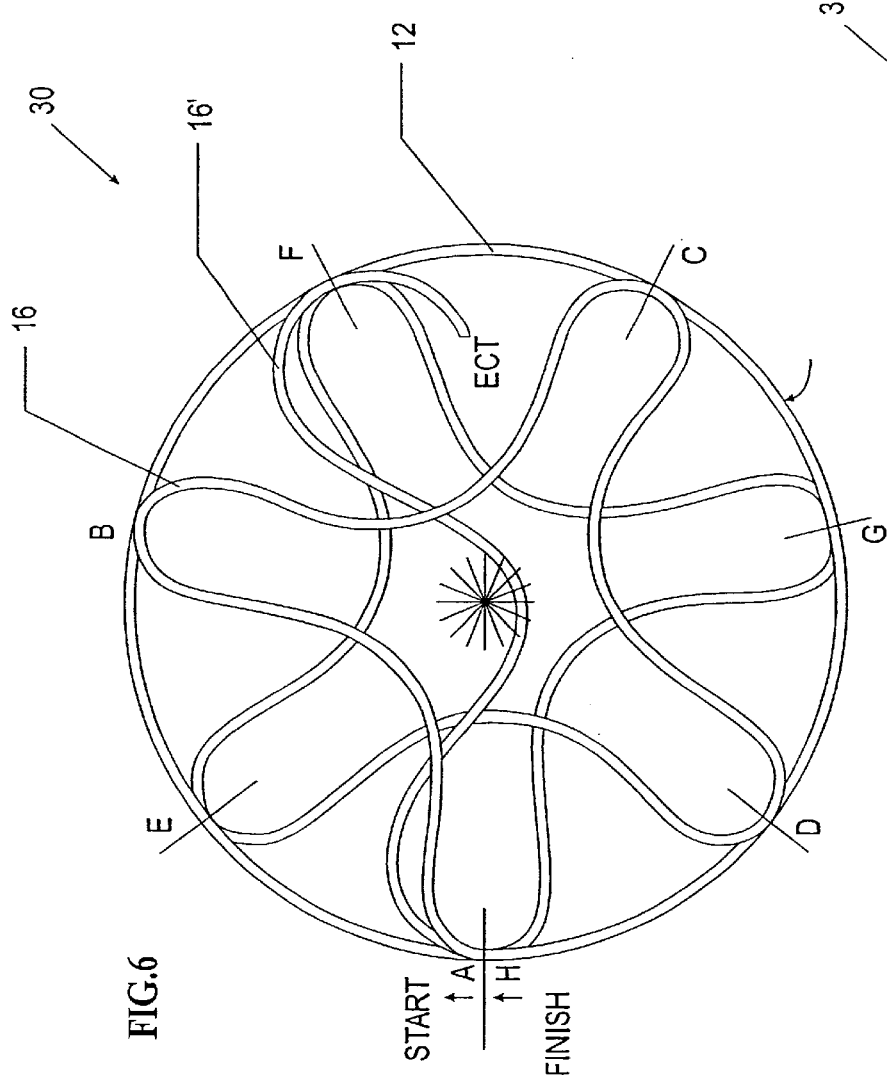
FIG. 6 is a plan view of an alternative implementation of the intravascular filter of the present invention.
Figure 7:
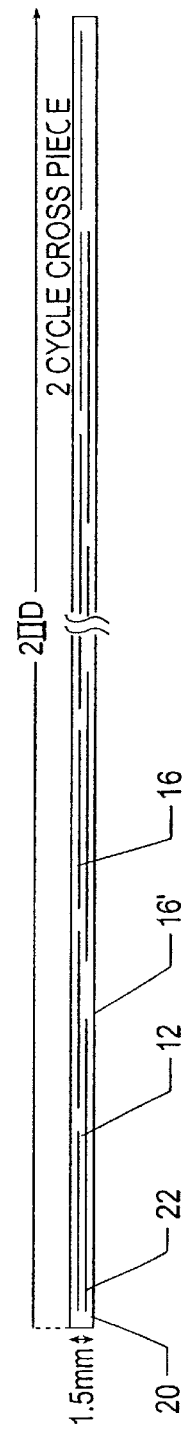
FIG. 7 is a schematic plan view of the device of FIG. 6 prepared as a straight strip prior to deployment.

Turning now to FIGS. 6 and 7, there is shown an additional implementation of an intravascular filter, generally designated 30, constructed and operative according to the teachings of the present invention. Filter 30 is similar to filter 10 described above, but employs an additional flexible elongated member 16'. In this case, the filter pattern is based upon 7-fold symmetry (p=7). The second elongated member 16 is arranged in a pattern with its seven lobes spaced around two turns of the helix (n=2, with an angular period of $4\pi/7$ radians or 102.86°) bridging the sequence of points A, B, C, D (first turn), E, F, G and H (second turn). The additional elongated member 16' has its lobes spaced according to a three-turn cycle (n=3, with an angular period of $6\pi/7$ radians or 154.29°) bridging the sequence of points A, F, D (first turn), B and G (second turn). For clarity of presentation, only one lobe of the latter angular frequency has been shown. Although the latter pattern is incomplete after the two turns provided by this example, the first two turns typically provide sufficient coverage for most applications, although consideration may have to be taken of the effects of the resulting asymmetry on fluid flow properties. Specifically, this configuration is believed to be effective to provide a filter size in the range of about 3–4 mm for a blood vessel of diameter up to about 30 mm. Where finer filtering is required, the pattern may be extended to a third turn.

In this context, it should be noted that the filter structures of the present invention may advantageously be manufactured as an elongated strip or other elongated configuration corresponding to numerous turns of the filter structure. The strip is then cut to a length corresponding to a helical filter structure with the appropriate number of turns to provide the required filtering characteristics for a given application.

FIG. 7 shows the implementation of FIG. 6 in its fully straightened form according to the preferred strip implementation described above. In the case shown here, first elongated member 12 is provided as a middle element with elongated members 16 and 16' connected either side. It should be noted, however, that the connection of the elongated elements making up the filter to the helical backbone is not necessarily direct. Thus, in an alternative example (not shown), elongated member 16 may be connected at points of intersection (or at its extremities only) to elongated member 16' which is, in turn, connected to first elongated member 12.

The dimensions of the filters of the present invention may clearly be varied according to the intended application. For most IVC applications, a filter diameter of between 18 and 30 mm is appropriate. The total straightened length of the filter for a two-turn helix is then $2\pi$ times this diameter, i.e., typically between about 110 and about 190 mm.

The transverse dimensions of the elongated members used are preferably in the region of about 0.5 mm. As a result, the maximum transverse dimension of the delivery means for filters 10 and 30 formed from two or three elements is typically slightly greater than 1 mm or 1.5 mm, respectively. This offers greatly reduced trauma compared to the 3 mm delivery systems required by many of the prior art devices. In certain cases, it may be possible to reduce the diameter of the catheter even further by optimizing packing of the cross-pieces and backbone, and/or by suitable choice of cross-sectional shape of the individual members. For example, if the filter of FIG. 6 is made from three separate wires, the wires can be of circular cross-section, packed together as a triad inside a circular catheter of diameter slightly greater than 1 mm. Additional factors affecting the choice of cross-sectional shape of the members are the desired fluid dynamic properties when the filter is deployed.

At this stage, the operation of the filters of the present invention will be clearly understood. The filter is put in place in the vessel by a tailored delivery system, such as a special form of catheter. The end of the delivery system is positioned inside the vessel at the desired point of deployment. The filter is then pushed from the end by suitable means, such that the portion which emerges reverts from its straightened form to its helical profile and presses itself outwards against the vessel's walls. The cross-pieces simultaneously take on their memory curved shape. The cross-pieces bow radially inwards and may, to a small extent, bow axially in the direction of fluid flow, forming a cup type profile when viewed normal to the vessel as in FIG. 4. This helps prevent tangling as the filter unfolds from the delivery system.

The helix can also be retracted back into a tailored retrieval system inserted into the vessel. Specifically, the helical backbone and bowed cross-pieces collapse back into a straightened form when pulled at the backbone's end. Pulling may be achieved by hooking the backbone with a suitable tool, or by screwing a pulling device onto a thread formed on the backbone's end.

Figure 8:
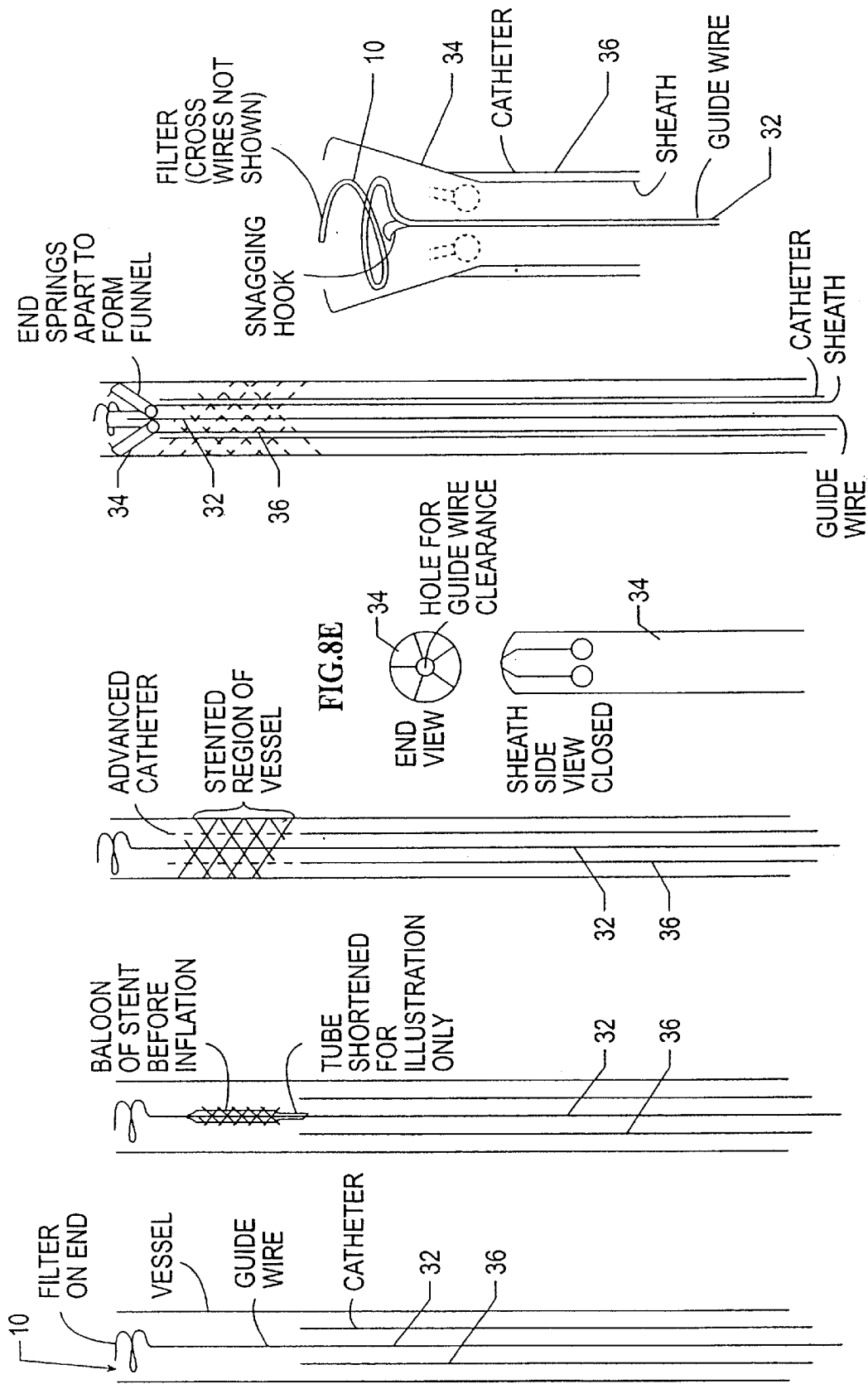
FIGS. 8A–8C are schematic cross-sectional views illustrating stages of a stenting procedure performed according to the teachings of the present invention using distal protection provided by an intravascular filter.
FIG. 8D is a schematic side view of a withdrawal sheath, for use in retrieval of the intravascular filter of FIGS. 8A–8C, shown in a closed state.
FIG. 8E is an end view of the withdrawal sheath of FIG. 8D.
FIG. 8F is a schematic cross-sectional view similar to FIGS. 8A–8C showing the use of the withdrawal sheath of FIG. 8D to withdraw the intravascular filter.
FIG. 8G is an enlarged view of the open end of the withdrawal sheath of FIG. 8F.
Figure 9:
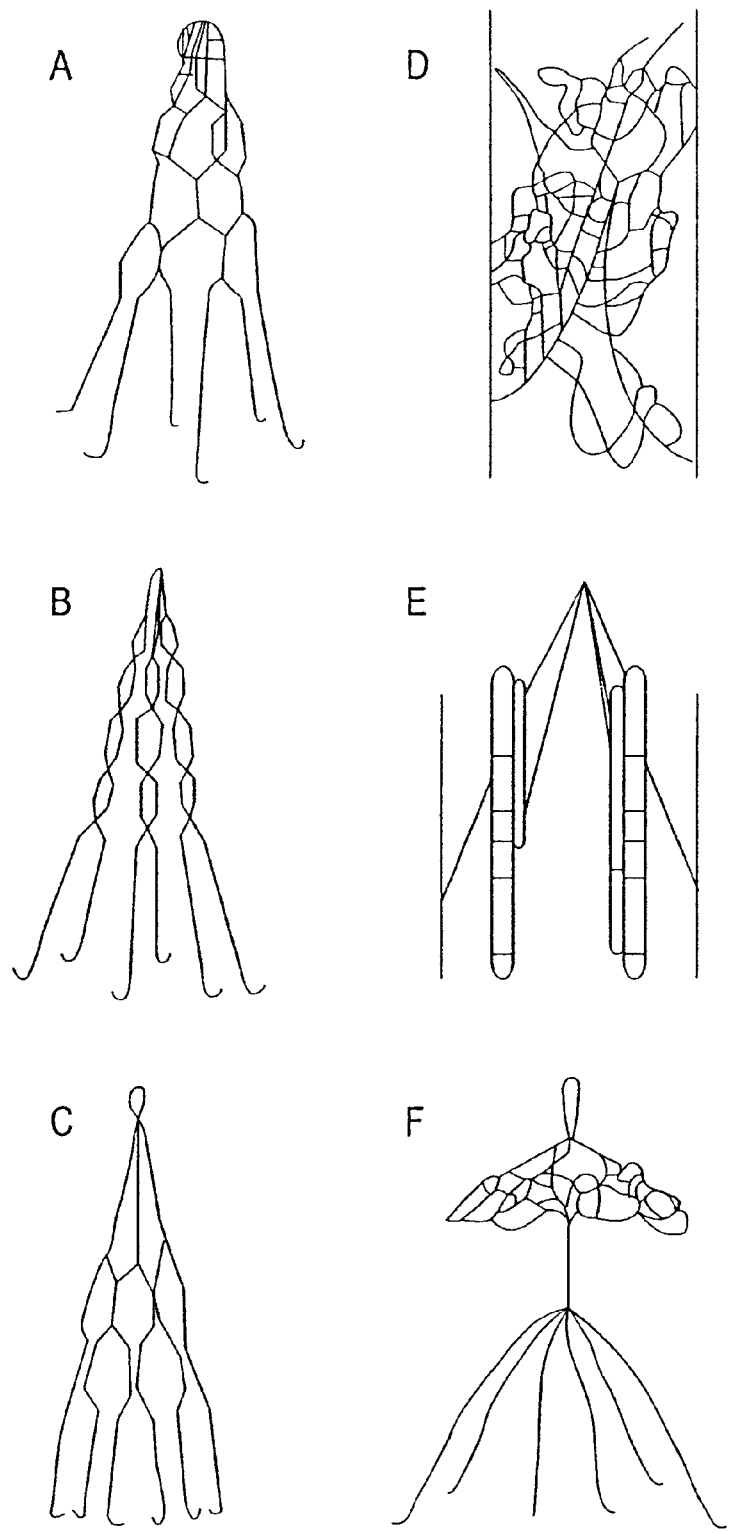
FIG. 9 is a schematic representation of a number of conventional IVC filters currently in use.

By way of a practical example, FIGS. 8A–8G illustrate the use of an intravascular filter of the present invention in a distal protection application. In this case, as mentioned above, filter 10 is preferably attached to the end of a guidewire 32 and is deployed distally of the region of the vessel to be stented and the procedure is performed (FIGS. 8A–8C), catching any debris which may be released from the area of narrowing. For clarity of presentation, cross-pieces 16 have been omitted. At the end of the procedure, the filter may be withdrawn in a certain way to retain the debris and extract the filter and debris through the catheter. A preferred method is to advance a sheath 34 around guidewire 32 into the catheter 36 and through the stent. The end of the cylindrical sheath 34 is previously prepared by shaped cuts along its length for a certain length to form a number of independent pieces, and the end of those pieces rolled inwards to form a retainer for both filter and debris. A depiction of a sheath end which has been cut five ways is shown in FIGS. 8D and 8E. The prepared end of the sheath fans out to the dimension of the vessel when no longer constrained by the catheter to form a funnel (FIGS. 8F and 8G), and the shaped cuts allow the continued passage of fluid through the vessel. The sheath may be advanced towards the filter, which simultaneously may be retracted into the funneled end. As the entire assembly is then retracted into the catheter, the funneled end aids in crushing the filter symmetrically, the rolled ends of the shaped end pieces preventing the filter mass from escaping. The symmetrical crushing and continued retraction of the guide wire and filter ensure it collapses inside the sheath to retain as much debris as possible. The collapse of the filter material which is designed to be weaker than the sheath material, may be further aided by a hook fashioned on the guide wire where the filter joins. Once caught in the funneled end of the sheath, the guide wire may be pushed while the sheath is simultaneously retracted, such that the hook catches member 16 of the filter to further aid its collapse within the sheath. The sheath is preferably made from a material of high tensile strength and sufficient springiness for the purposes described above.

It will be appreciated that the above descriptions are intended only to serve as examples, and that many other embodiments are possible within the spirit and the scope of the present invention.

What is claimed is:

1. An intravascular filter for minimally invasive deployment within a vessel so as to obstruct the passage of particles of dimensions greater than a predefined value through the vessel, the intravascular filter comprising:

(a) a first flexible elongated member configured to assume a substantially helical form extending for at least about one turn about a central axis; and (b) at least a second flexible elongated member connected to said first flexible elongated member at least two spaced apart connection positions chosen such that approximately equal lengths of said first and second flexible elongated members lie between said connection positions, said second flexible elongated member being configured to assume a predefined filter form lying substantially within said substantially helical form in such a manner as to form an obstacle to passage through said substantially helical configuration, in a direction parallel to said central axis, of particles having dimensions greater than the predefined value.

2. The intravascular filter of claim 1, wherein at least one of said first and second flexible elongated members is attached to, or integrally formed with, a guidewire in such a manner that the intravascular filter can be drawn into a catheter by withdrawal of said guidewire.

3. The intravascular filter of claim 1, wherein said predefined filter form is substantially angularly periodic about said central axis.

4. The intravascular filter of claim 1, wherein said predefined filter form includes a plurality of lobes angularly spaced around said central axis.

5. The intravascular filter of claim 1, wherein said substantially helical form approximates to a helix modulated by an undulating pattern having a maximum amplitude not significantly greater than a diameter of said helix.

6. The intravascular filter of claim 1, wherein said first flexible elongated member is formed with a plurality of small longitudinal slits and is configured to open up said slits to form a latticework type effect when in said substantially helical form.

7. The intravascular filter of claim 1, wherein said first and second flexible elongated members are formed as an elongated flat strip subdivided along its length by an elongated slit except at said connection positions.

8. The intravascular filter of claim 1, wherein said first and second flexible elongated members are formed as two lengths of wire connected together at said connection positions.

9. The intravascular filter of claim 1, wherein said first and second flexible elongated members are formed primarily from a super elastic alloy, said first and second flexible elongated members being elastically biased to said substantially helical form and said filter form, respectively, and being elastically deformable into a substantially straight configuration in which said first and said second flexible elongated members are substantially straight to facilitate minimally invasive deployment.

10. The intravascular filter of claim 1, wherein said first and second flexible elongated members are formed primarily from a shape-memory material, said first and second flexible elongated members being set to said substantially helical form and said filter form, respectively, and being subsequently deformed to provide a substantially straight configuration in which said first and said second flexible elongated members are substantially straight to facilitate minimally invasive deployment.

11. The intravascular filter of claim 10, wherein, subsequent to a transition from said substantially straight state to said pre-set state, said first and second flexible are deformable so as to return to a substantially straight state to facilitate minimally invasive retrieval.

12. The intravascular filter of claim 1, wherein said first and second flexible elongated members are formed primarily from Nitinol.

13. The intravascular filter of claim 1, further comprising at least a third flexible elongated member connected to said first flexible elongated member at at least two spaced apart connection positions chosen such that approximately equal lengths of said first and third flexible elongated members lie between said connection positions, said third flexible elongated member being configured to assume an additional predefined filter form lying substantially within said substantially helical form and configured to complement said filter form of said second elongated member so as to form an enhanced obstacle to passage through said substantially helical configuration, in a direction parallel to said central axis, of particles having dimensions greater than the predefined value, wherein said first, second and third flexible elongated members are prepared in a substantially straight configuration to facilitate minimally invasive deployment.

14. An intravascular filter for minimally invasive deployment within a vessel so as to obstruct the passage of particles of dimensions greater than a predefined value through the vessel, the intravascular filter comprising:
  (a) a first flexible elongated member configured to assume a substantially helical form extending for at least about one turn about a central axis; and
  (b) second and third flexible elongated members, each connected to said first flexible elongated member at least two spaced apart connection positions, wherein said second flexible elongated member is configured to assume a first predefined filter form lying substantially within said substantially helical form and said third flexible elongated member is configured to assume a second predefined filter form lying substantially within said substantially helical form, said first and second predefined filter forms together forming an obstacle to passage through said substantially helical configuration, in a direction parallel to said central axis, of particles having dimensions greater than the predefined value.

15. The intravascular filter of claim 14, wherein said first predefined filter form is substantially angularly periodic with a first angular period about said central axis and said second predefined filter form is substantially angularly periodic with a second angular period about said central axis, said second angular period differing from said first angular period.

16. The intravascular filter of claim 14, wherein said first, second and third flexible elongated members are formed as an elongated flat strip subdivided along its length by two elongated slits except at said connection positions.

17. The intravascular filter of claim 14, wherein said first, second and third flexible elongated members are formed as three lengths of wire connected together at said connection positions.

18. The intravascular filter of claim 14, wherein said first, second and third flexible elongated members are formed primarily from a super elastic alloy, said first, second and third flexible elongated members being elastically biased to said substantially helical form and said first and second filter forms, respectively, and being elastically deformable into a substantially straight configuration in which said first, second and third flexible elongated members are substantially straight to facilitate minimally invasive deployment.

19. The intravascular filter of claim 14, wherein said first, second and third flexible elongated members are formed primarily from a shape-memory material, said first, second and third flexible elongated members being set to said substantially helical form and said first and second filter forms, respectively, and being subsequently deformed to provide a substantially straight configuration in which said first, second and third flexible elongated members are substantially straight to facilitate minimally invasive deployment.

20. The intravascular filter of claim 14, wherein said first, second and third flexible elongated members are formed primarily from Nitinol.

21. A method for preparing an intravascular filter for use, the method comprising:
  (a) providing an elongated strip including:
    (i) a first flexible elongated member configured to assume a substantially helical form extending for a plurality of turns about a central axis, and
    (ii) at least a second flexible elongated member connected to said first flexible elongated member at least one connection position per turn of the helical form, the connection positions being chosen such that approximately equal lengths of said first and second flexible elongated members lie between said connection positions, said second flexible elongated member being configured to assume a predefined filter form lying substantially within said substantially helical form in such a manner as to form an obstacle to passage through said substantially helical configuration, in a direction parallel to said central axis, of particles having dimensions greater than the predefined value, wherein said first and said second flexible elongated members are prepared in a substantially straight configuration to facilitate minimally invasive deployment; and (b) cutting said elongated strip to separate a given length of said elongated strip to provide an intravascular filter ready for minimally invasive deployment.

* * * * *